United States Patent
Möller et al.

(10) Patent No.: US 7,199,270 B2
(45) Date of Patent: Apr. 3, 2007

(54) METHOD FOR THE SEPARATION OF METHYL MERCAPTAN FROM REACTION GAS MIXTURES

(75) Inventors: Alexander Möller, Gelnhausen (DE); Wolfgang Böck, Langenselbold (DE); Stephan Rautenberg, Bornheim (DE); Hans-Joachim Hasselbach, Gelnhausen (DE); Wolfgang Taugner, Altenstadt (DE); Harald Heinzel, Altenstadt (DE); Theo Zarfl, Wesseling (DE)

(73) Assignee: Degussa AG, Düsseldorf (DE)

( * ) Notice: Subject to any disclaimer, the term of this patent is extended or adjusted under 35 U.S.C. 154(b) by 132 days.

(21) Appl. No.: 11/016,130

(22) Filed: Dec. 17, 2004

(65) Prior Publication Data

US 2005/0137426 A1   Jun. 23, 2005

(30) Foreign Application Priority Data

Dec. 18, 2003   (DE)   ................. 103 59 636

(51) Int. Cl.
C07C 319/00   (2006.01)
(52) U.S. Cl. ........................................ 568/71
(58) Field of Classification Search ............ 568/71
See application file for complete search history.

(56) References Cited

U.S. PATENT DOCUMENTS

| | | | |
|---|---|---|---|
| 2,626,282 A | 1/1953 | Cunningham et al. | |
| 3,438,868 A | 4/1969 | Sawaki et al. | |
| 5,866,721 A | * 2/1999 | Hofen et al. | 568/71 |
| 5,886,230 A | * 3/1999 | Hofen et al. | 568/71 |
| 5,905,171 A | * 5/1999 | Hsu | 568/41 |

FOREIGN PATENT DOCUMENTS

| | | |
|---|---|---|
| DE | 1 768 826 | 8/1971 |
| DE | 1 618 884 | 9/1971 |
| DE | 2 320 544 | 9/1974 |
| EP | 0 850 922 A1 | 7/1998 |
| EP | 0 850 923 A1 | 7/1998 |
| FR | 1 520 328 | 4/1968 |
| GB | 1166961 | 10/1969 |

* cited by examiner

Primary Examiner—James O. Wilson
Assistant Examiner—Chukwuma Nwaonicha
(74) Attorney, Agent, or Firm—Smith, Gambrell & Russell, LLP

(57) ABSTRACT

The invention relates to a method for the separation of methyl mercaptan from reaction gas mixtures obtained by means of the catalytic conversion of H2S with methanol, by means of converting the methyl mercaptan into MMP in the presence of the byproducts with acrolein, and separating the same.

16 Claims, 1 Drawing Sheet

METHOD FOR THE SEPARATION OF METHYL MERCAPTAN FROM REACTION GAS MIXTURES

INTRODUCTION AND BACKGROUND

The invention relates to a method for the separation of methyl mercaptan from reaction gas mixtures obtained by means of catalytic conversion of H2S with methanol.

Methyl mercaptan is an industrially important precursor for the synthesis of the nutritive amino acid methionine, or the hydroxianalogous 2-hydroxi-4-methyl mercaptobutyric acid (MHA), as well as for the production of dimethyl sulfoxide and dimethyl sulfone. Today, it is predominantly produced from methanol and hydrogen sulfide by means of the conversion onto a catalyst of alumina. The synthesis of methyl mercaptan usually occurs in the gas phase at temperatures between 300 and 500° C., and at pressures between 14.5 and 362.59 psi (1 and 25 bar). In order to increase the activity and selectivity of the catalyst, the same is usually coated with potassium woiframate as the promoter. The conversion of hydrogen sulfide and methanol into methyl mercaptan is an exothermic process, in which 28,500 KJ are released per kilomols of converted methanol. One method is described, for example, in EP 0 850 923 B.

In addition to the desired methyl mercaptan, the product gas mixture of the synthesis also contains the water created during the reaction, and as the byproducts, dimethyl sulfide, dimethyl ether, low-amounts of polysulfide, such as dimethyl disulfide, as well as non-converted methanol, excess hydrogen sulfide, and the inert gases nitrogen, carbon dioxide, carbon monoxide, and hydrogen in terms of the reaction. The separation of the product gas mixtures into their components serves for the extraction of methyl mercaptan and dimethyl sulfide, for the discharge of water and inert gas components, as well as for the return of the unused methanol and hydrogen sulfide into the synthesis reactor.

DE-PS 17 68 826 relates to a method for separation, in which the product gas mixture is distilled at a pressure of not more than 159.5 psi (11 bar), and at a temperature of 10 to 140° C. The gaseous phase of this distillation essentially consists of hydrogen sulfide, inert gases, dimethyl sulfide, and methyl mercaptan. Methyl mercaptan and dimethyl sulfide are eluted in counterflow from the gaseous phase with methanol. The remaining hydrogen sulfide and the inert gases are returned to the synthesis reactor as cycle gas. The loaded elution methanol is again processed by distillation together with the practically hydrogen sulfide free sump of the distillation, and also returned to the manufacturing process.

An improved method having a higher definition in the separation of the product gas mixtures in the individual flow of the matter is described in EP 0 850 923 B (U.S. Pat. No. 5,866,721).

In addition to the high investment and operating costs (columns of 40 theoretical steps with a nominal pressure level of 232 psi (16 bar) are usually required, wherein the nominal pressure level is a measure for the stability of the reactor used), one disadvantage of this processing by distillation of the complex reaction mixture is the inevitable formation of residue that must be disposed of, and as a consequence thereof, the loss of resources. Additionally, a 2-phase mixture of water and sulfur compounds may occur during processing by means of. distillation of the said reaction mixture in the sump, which makes the controlling of the column substantially more difficult. In addition to environmental pollution, the further processing of methyl mercaptan without the separation of the said admixtures, however, may lead to substantial product failures in the production of the subsequent product, such as methionine, thus making separation unavoidable.

SUMMARY OF THE INVENTION

It is the task of the invention to provide a method, with which the high distillation efforts for the extraction of pure methyl mercaptan can be avoided, but the methyl mercaptan obtained in the catalytic conversion of H2S with methanol can still be used for additional conversions without any losses.

The subject of the invention is a method for the separation of methyl mercaptan from reaction mixtures created with the catalytic conversion of H2S with methanol, characterized in that 1.1 the components of non-converted H2S and methanol, as well as the water obtained in the reaction mixture, are separated, 1.2 the raw methyl mercaptan obtained is subsequently converted with 3-methyl mercaptopionaldehyde (MMP) and acrolein, or converted into MMP solely with acrolein in the presence of a catalyst, and 1.3 the components from the methyl mercaptan synthesis still present in the reaction mixture are separated from the MMP in a distillation process.

BRIEF DESCRIPTION OF DRAWING

The accompanying drawing shows a flow diagram of the method of the invention.

DETAILED DESCRIPTION OF INVENTION

Figure 1:
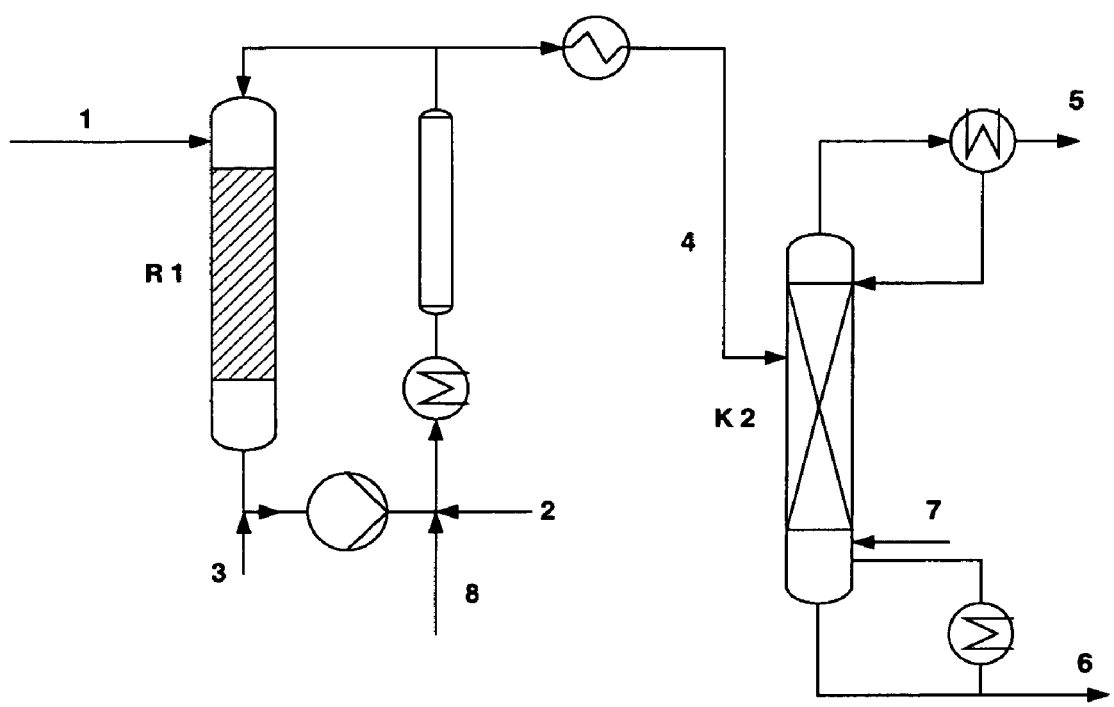

Advantageously, the components are stripped by means of charging of an inert entrainer. The column is operated at 14.5 to 72.5 psi (1 to 5 bar), particularly at 14.5 to 43.5 psi (1 to 3 bar), and between 90 and 135° C., particularly at 14.5 to 36.25 psi (1 to 2.5 bar).

Nitrogen, carbon dioxide, or steam, are particularly suitable as the entrainer.

Contrary to the subsequent synthesis steps for the production of methionine, the conversions of methyl mercaptan with MMP and acrolein are not influenced by the byproducts from the production of methyl mercaptan. According to the invention, the complicated isolation of this compound (according to EP 0 850 923 approximately 40 theoretical bottoms in the distillation columns) can be avoided. Distillation columns with 9 to 20 theoretical bottoms, advantageously 10 to 15 bottoms, usually suffice for the separation of the byproducts from the created, and possibly initially added, aldehyde MMP, wherein 87 psi (6 bar) is usually advantageously selected as the nominal pressure level. Furthermore, a loss of mercaptan is avoided, and the handling time of mercaptan that is registered as a dangerous substance, is shortened.

The MMP formation from methyl mercaptan and acrolein in the presence of a catalyst is known in prior art as a two-stage process with the use of the pure parent compounds (DE 1 618 884 B, DE 2 320 544 B).

For example, mercaptan with a purity of 99.5% is used in DE 1 618 884 B. According to the invention, however, raw methyl mercaptan with a methyl mercaptan content of approximately 93 wt-%, with a simultaneous content of 1.5 to 5 wt-% of dimethyl disulfide, 0.5 to 3 wt-% of dimethyl ether, and approximately 1 wt-% of water and traces of methanol may also be used, with the total sum being 100%.

For this purpose, the methyl mercaptan can be charged into an MMP either in gaseous, or liquid form, preferably at a pressure of 14.5 to 145 psi (1 to 10 bar), preferably in a cycle-operated reactor.

Methyl mercaptan and MMP are used at a molar ratio of 1 to at least 1, particularly 1 to 30.

The temperature of the reaction leading to the formation of hemithioacetal or thioacetal is between 50 and 120° C., particularly between 65 and 110° C. Subsequently, the reaction product obtained is converted with acrolein in the presence of a catalyst.

The applied reaction conditions are practically the same as those in the first step. An excess of acrolein is advantageous. The suitable catalysts are known in prior art.

Usually, organic peroxides, organic bases, mixtures of organic acids and bases, such as acetic acid and pyridine, are used. The method may be operated continuously, semi-continuously, or batch-by-batch.

One variation of the separation method is the converting of the raw methyl mercaptan into MMP in a reaction loop with acrolein with the admixture of a suitable catalyst, and removing the respective inert admixtures as described above.

The product obtain can now be directly added, for example, to the methionine synthesis, or to its analogous compounds, such as MHA, filled into standardized fueling vehicles, and conveyed, or transported to a common fuel depot.

EXAMPLE

The invention is described by the flow chart (FIG. 1) as follows:

The raw methyl mercaptan obtained, for example, in accordance with EP 0850923, of the following composition: methyl mercaptan~93 wt-%, dimethyl sulfide~4.5 wt-%, dimethyl ether~1.5 wt-%, water~1 wt-%, and traces of methanol or methyl mercaptan~93 wt-%, dimethyl sulfide 1.5–5 wt-%, dimethyl disulfide 0.2–1 wt-%, dimethyl ether 0.5–3 wt-%, water~1 wt-%, and traces of methanol, is added (in gaseous and/or liquid form) via 1 or 8 to a reactor R 1 operated in cycles at pressures between 14.5 and 72.5 psi (1 and 5 bar), and a temperature, such as is described in DE 2320544 between 50 and 120° C. with MMP. The supplying of acrolein, which is required for the conversion into MMP, occurs by means of the strand 2, and the admixture of a respective catalyst (mixture of pyridine and acetic acid, such as is described in FR 1520328, or other mixtures of organic bases and organic acids) via 3. The reaction mixture subsequently is then separated via 4 in column K 2 (number of theoretical bottoms: 0.15 . . . ) from its inert compounds of the said aldehydes at a pressure of 14.5–43.5 psi (⅓ bar), and a temperature of between 90 and 135° C., and these are added via 5 for further use. If necessary, the removal of the undesired admixtures can be further improved by the additional chare of an inert entrainer via 7, such as nitrogen, carbon dioxide, or steam, preferably nitrogen. The product obtained is added via 6 for its further use. Based on the raw methyl mercaptan used, the isolation yield is quasi quantitative, i.e. >99.9%.

The invention claimed is:

1. Method for the separation of methyl mercaptan from a reaction mixture created in the catalytic conversion of $H_2S$ with methanol, comprising:

1.1 separating portions of non-converted $H_2S$ and methanol, as well as the water contained in the reaction mixture to obtain crude methyl mercaptan, 1.2 subsequently converting the crude methyl mercaptan by reacting with 3-methyl mercaptopropionaldehyde (MMP) and acrolein into MMP, or converting the crude methyl mercaptan into MMP solely by reacting with acrolein in the presence of a catalyst, and 1.3 separating byproducts from the methyl mercaptan synthesis still present in the reaction mixture after MMP synthesis from said mixture by distilling.

2. Method according to claim 1, wherein the components are stripped by means of charging an inert entrainer.

3. Method according to claim 2, wherein nitrogen, carbon dioxide, or steam are used as the inert entrainer.

4. Method according to claim 1, wherein the components are separated at a pressure of 14.5 to 72.5 psi (1 to 5 bar), within a temperature range of 90 to 135° C.

5. Method according to claim 1, wherein a distillation column with less than 20 bottoms is used.

6. A method for the separation of methyl mercaptan from a methyl mercaptan synthesis reaction mixture created in the catalytic conversion of $H_2S$ with methanol, comprising:

separating portions of non-converted $H_2S$ and methanol, as well as water contained in the reaction mixture, to thereby obtain crude methyl mercaptan, subsequently converting the crude methyl mercaptan obtained with 3-methyl mercaptopropionaldehyde (MMP) and acrolein to form MMP, or converting the crude methylmercaptan into MMP solely with acrolein in the presence of a catalyst, and distilling components from the methyl mercaptan synthesis still present in the reaction mixture to separate said components from the MMP in a distillation process.

7. The method according to claim 6, further comprising introducing an inert entrainer in the distillation process.

8. The method according to claim 7, wherein the inert entrainer is a member selected from the group consisting of nitrogen, carbon dioxide, and steam.

9. The method according to claim 6, wherein the components are separated at a pressure of 14.5 to 72.5 psi (1 to 5 bar), within a temperature range of 90 to 135° C.

10. The method according to claim 7, wherein the components are separated at a pressure of 14.5 to 72.5 psi (1 to 5 bar), within a temperature range of 90 to 135° C.

11. The method according to claim 8, wherein the components are separated at a pressure of 14.5 to 72.5 psi (1 to 5 bar), within a temperature range of 90 to 135° C.

12. Method according to claim 6, wherein a distillation column with less than 20 bottoms is used.

13. Method according to claim 7, wherein a distillation column with less than 20 bottoms is used.

14. Method according to claim 8, wherein a distillation column with less than 20 bottoms is used.

15. Method according to claim 9, wherein a distillation column with less than 20 bottoms is used.

16. The process according to claim 1 wherein at least one member from the group consisting of dimethylsulfide, diinethylether, polysulfide, methanol, hydrogen sulfide or inert gas is removed as a by-product.

* * * * *